United States Patent [19]

Habuka et al.

[11] Patent Number: 5,318,900
[45] Date of Patent: Jun. 7, 1994

[54] METHOD FOR PRODUCING ANTIVIRAL PROTEIN UTILIZING E. COLI TRANSFORMANT, AND GENE AND E. COLI VECTOR USED IN THE METHOD

[75] Inventors: Noriyuki Habuka; Kiyotaka Akiyama; Hideaki Tsuge; Takashi Matsumoto; Masana Noma, all of Yokohama, Japan

[73] Assignee: Japan Tobacco Inc., Tokyo, Japan

[21] Appl. No.: 958,452

[22] Filed: Oct. 7, 1992

Related U.S. Application Data

[63] Continuation of Ser. No. 566,570, Aug. 13, 1990, abandoned.

[30] Foreign Application Priority Data

Aug. 17, 1989 [JP] Japan ................... 1-210767

[51] Int. Cl.$^5$ ............... C07K 15/10; C12N 15/29; C12N 15/70; C12P 1/04
[52] U.S. Cl. ............... 435/69.8; 435/252.33; 435/320.1; 530/370; 536/23.6; 536/24.1; 935/48
[58] Field of Search ........... 435/69.1, 69.8, 172.3, 435/252.33, 320.1; 530/350, 370; 536/23.6, 24.1; 935/29, 27, 41, 48

[56] References Cited

U.S. PATENT DOCUMENTS

4,757,013  7/1988  Inouye ............... 435/172.3

FOREIGN PATENT DOCUMENTS

314184  5/1989  European Pat. Off. .

OTHER PUBLICATIONS

Habuka et al., Journal of Biological Chemistry, vol. 265, No. 19, pp. 10988–10992, Jul. 5, 1990.
Hussain, et al., Federation of European Biochemical Societies, vol. 244, No. 2, pp. 383–387, Feb. 27, 1989.
Proc. Natl. Acad. Sci. U.S.A., vol. 83, pp. 4109–4113, Jun. 1986, Biochemistry Tokino et al., "Purification and Properties of the Mini-F Plasmid . . . ".
The Journal of Biological Chemistry, vol. 264, No. 12, Issue of Apr. 25, 1989, Habuka et al., pp. 6629–6637, "Amino Acid Sequence of Mirabilis . . . ".
Mol. Gen. Genet, (1982), 187:79–86, Tsurimoto et al., "Bacteriophage Lambda Initiators: Preparation from a Strain that Overproduces . . . ".
The Journal of Biological Chemistry, vol. 255, No. 1, Jan. 10, 1980 pp. 27–29, Movva et al., "Amino Acid Sequence of the Signal . . . ".
Habuka, N. et al., J. Biol. Chem. 264(12):6629–6637 (1989).
Takahara, M. et al. J. Biol. Chem. 260(5):2670–2674 (1985).
Becker, G. W. "Expression, Secretion and Folding of Human Growth Hormon in E. coli," FEBS 204:145–150 (1986).
Pouwels, P. H. Cloning Vectors: A Laboratory Manual, p. I–B–i–5 (1985).

Primary Examiner—Robert A. Wax
Assistant Examiner—Dian C. Jacobson
Attorney, Agent, or Firm—Nixon & Vanderhye

[57] ABSTRACT

A method for producing MAP utilizing a gene which is formed by combining a gene coding for E.coli outer membrane protein OmpA signal peptide upstream of MAP gene as a foreign gene. In this method, said gene is inserted in a plasmid having E.coli expression systems and the recombinant plasmid obtained is introduced into E.coli for transformation.

4 Claims, 5 Drawing Sheets

Fig. 1

NdeI                                                           XbaI
MetLysLysThrAlaIleAlaIleAlaValAlaValAlaLeuAlaGlyPheAlaThrValAlaAlaGlnAla AlaProThrLeu

TATGAAAAAGACAGCTATCGCGATTGCAGTGGCACTGGCTGGTTTCGCTACTGTTGCTGCCCAGGCC GCGCCTACT
ACTTTTTCTGTCGATAGCGCTAACGTCACCGTGACCGACCAAAGCGATGGCATCCGCTCCGG CGCGGATGAGATC ompA signal         MAP

Fig. 3

EcoRI   PstI   SalI   SD     Nde I                                         XbaI       BanIII  HindIII AATTCCTGCAGGTCGACAGGAAACACATATGGCGCCTACTCTAGAAAAATCGATAAA
    GGACGTCCAGCTGTCCTTTGTGTATACCGCGGATGAGATCTTTTAGCTATTTTCGA

```
GCGCCTACTC TAGAAACCAT CGCTTCTCTG GACCTGAACA ACCCGACCAC CTACCTGTCT
CGCGGATGAG ATCTTTGGTA GCGAAGAGAC CTGGACTTGT TGGGCTGGTG GATGGACAGA

TTCATAACGA ATATCCGTAC GAAAGTCGCA GACAAAACCG AACAGTGTAC CATCCAGAAA
AAGTATTGCT TATAGGCATG CTTTCAGCGT CTGTTTTGGC TTGTCACATG GTAGGTCTTT

ATCTCTAAAA CCTTCACCCA GCGTTACTCT TACATAGACT TGATCGTGAG CTCGACGCAG
TAGAGATTTT GGAAGTGGGT CGCAATGAGA ATGTATCTGA ACTAGCACTC GACCTGCGTC

AAAATCACCC TAGCTATCGA CATGGCTGAC CTGTACGTTC TGGGTTACTC TGACATCGCT
TTTTAGTGGG ATCGATAGCT GTACCGACTG GACATGCAAG ACCCAATGAG ACTGTAGCGA

AATAACAAGG GTCGTGCTTT CTTCTTCAAA GACGTGACTG AGGCTGTTGC GAACAATTTC
TTATTGTTCC CAGCACGAAA GAAGAAGTTT CTGCACTGAC TCCGACAACG CTTGTTAAAG

TTCCCGGGAG CTACAGGTAC TAATCGTATC AAATTAACCT TTACAGGTTC TTATGGCGAT
AAGGGCCCTC GATGTCCATG ATTAGCATAG TTTAATTGGA AATGTCCAAG AATACCGCTA

CTCGAGAAAA ACGGCGGACT ACGTAAGGAC AATCCCCTAG GTATCTTCCG TCTGGAAAAC
GAGCTCTTTT TGCCGCCTGA TGCATTCCTG TTAGGGATC CATAGAAGGC AGACCTTTTG

TCGATAGTTA ACATTTATGG CAAAGCTGGT GACGTTAAAA AACAGGCTAA ATTCTTCTTA
AGCTATCAAT TGTAAATACC GTTTCGACCA CTGCAATTTT TTGTCCGATT TAAGAAGAAT

CTGGCTATCC AGATGGTTTC GGAGGCTGCG CGCTTTAAGT ATATCAGTGA CAAAATCCCG
GACCGATAGG TCTACCAAAG CCTCCGACGC GCGAAATTCA TATAGTCACT GTTTTAGGGC

TCTGAAAAAT ACGAAGAAGT TACCGTTGAC GAATACATGA CCGCTCTGGA AAACAACTGG
AGACTTTTTA TGCTTCTTCA ATGGCAACTG CTTATGTACT GGCGAGACCT TTTGTTGACC

GCTAAACTGT CTACGGCCGT ATACAACTCT AAGCCTTCTA CCACCACCGC TACCAAATGT
CGATTTGACA GATGCCGCCA TATGTTGAGA TTCGGAAGAT GGTGGTGGCG ATGGTTTACA

CAGCTGGCTA CCTCTCCCGT TACCATCTCT CCGTGGATAT TCAAAACCGT CGAGGAAATC
GTCGACCGAT GGAGAGGCCA ATGGTAGAGA GGCACCTATA AGTTTTGGCA GCTCCTTTAG

AAACTGGTTA TGGGTCTGCT TAAGTCTTCT TAATAA
TTTGACCAAT ACCCAGACGA ATTCAGAAGA ATTATT
```

Fig. 2

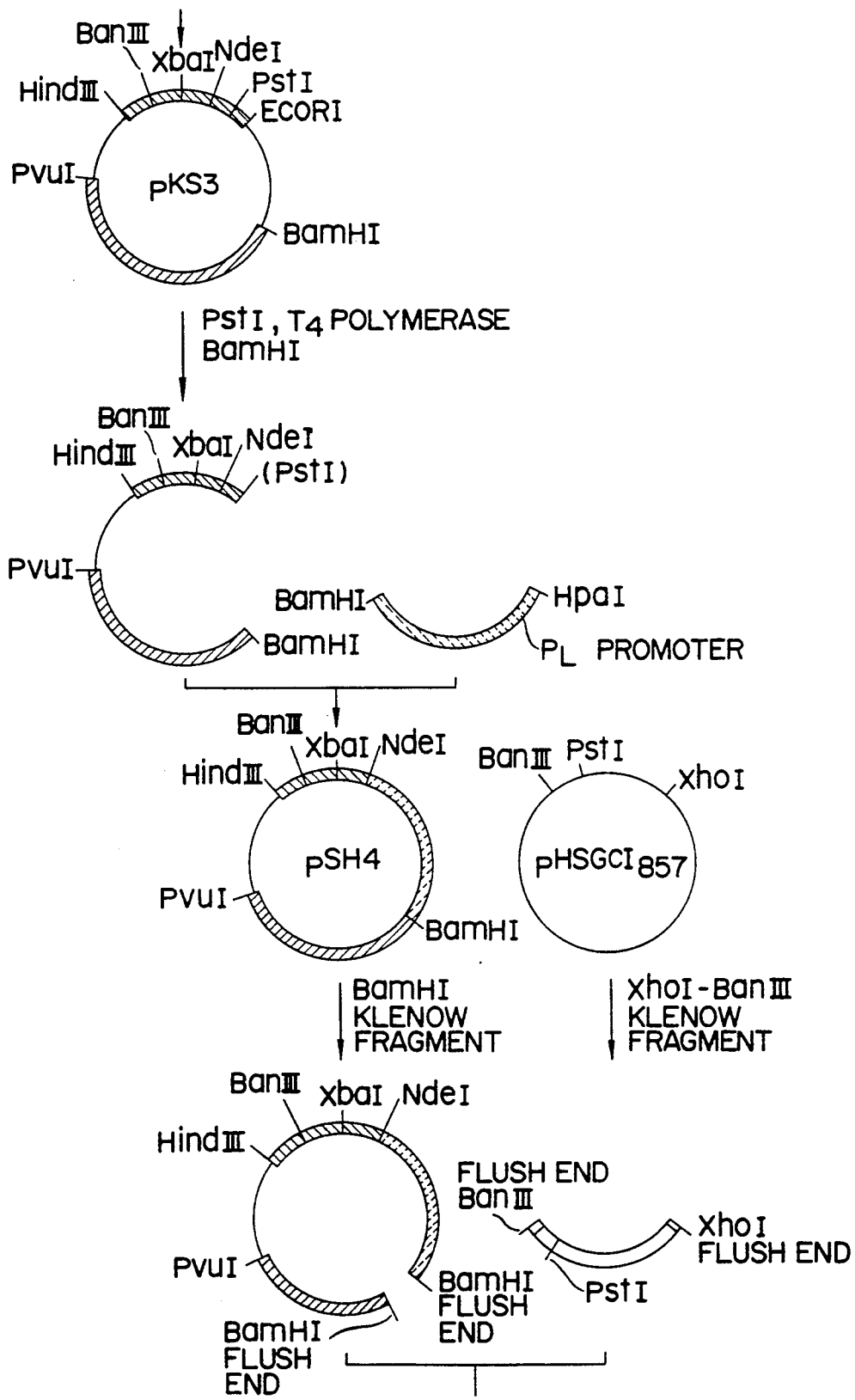
F I G. 4B

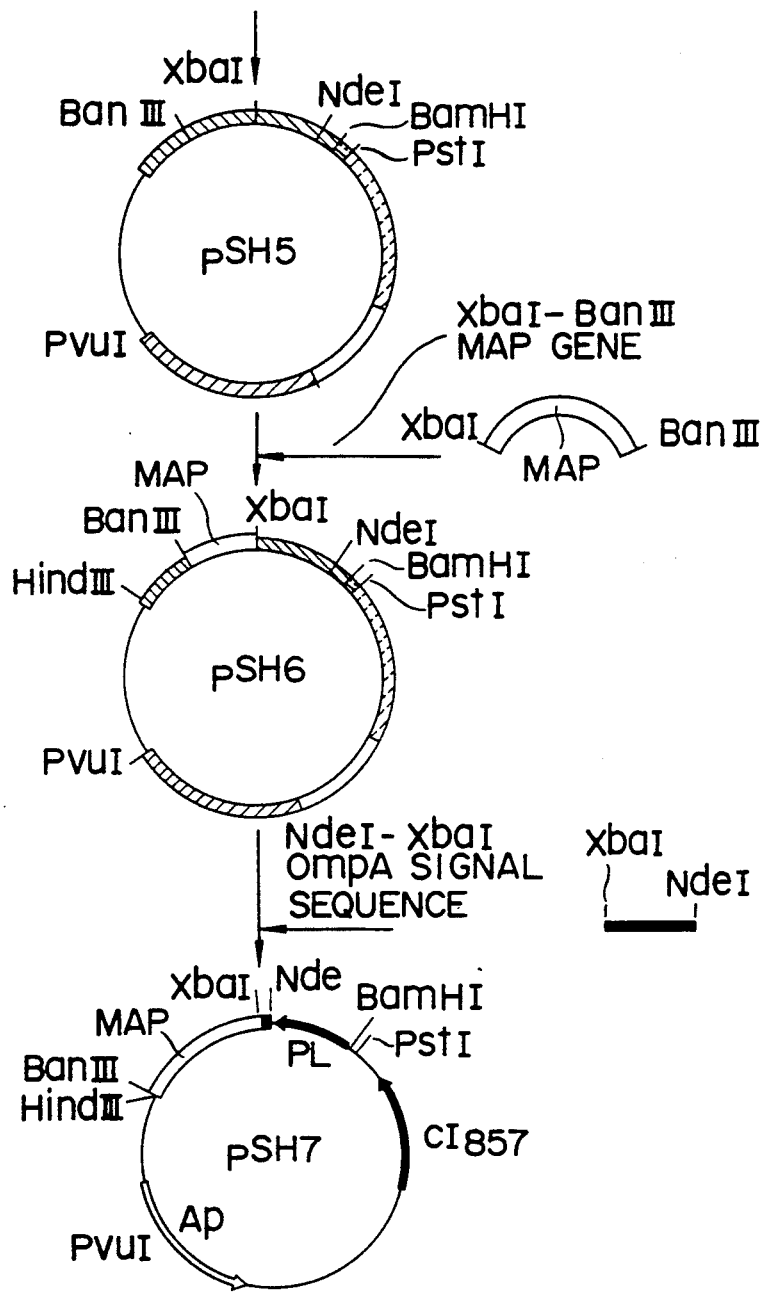
F I G. 4C

METHOD FOR PRODUCING ANTIVIRAL PROTEIN UTILIZING E. COLI TRANSFORMANT, AND GENE AND E. COLI VECTOR USED IN THE METHOD

This is a continuation of application Ser. no. 07/566,570, filed Aug. 13, 1990, now abandoned.

BACKGROUND OF THE INVENTION

1. Field of the Invention

This invention relates to a method for producing Mirabilis Antiviral Protein.

2. Description of the Related Art

Inventors of the present invention previously separated a novel basic protein from Mirabilis jalapa and found that this protein showed antiviral activity (Published Unexamined Japanese Patent Application No. 243100/85). Specifically, this protein is Mirabilis Antiviral Protein (hereafter abbreviated as MAP). The inventors also cultured tissues of Mirabilis jalapa and succeeded in production of MAP utilizing the cultured tissue (Published Unexamined Japanese Patent Application Nos. 125382/87 and 269710/86).

MAP can be mass-produced industrially and easily by growing a large amount of Mirabilis jalapa and extracting MAP therefrom. However, this method has the disadvantage that both much time and an extensive planted area are required for growing Mirabilis jalapa. Methods utilizing cultured tissue disclosed in said Published Unexamined Japanese Patent Application Nos. 125382/87 and 269710/86 also require a long period of approximately 12 days for cell culture.

Meanwhile, with a rapid improvement of gene manipulation techniques, cloning techniques, etc. in recent years, production of available substances using genetic engineering have been tried. Many trials have attained success. Additionally, in protein engineering, the genetic approach is becoming important to study novel proteins. This is due to improvements of analyzing techniques and DNA synthesis techniques which are accomplished by accumulating fundamental studies.

Under the circumstances as said, some trials have been made in the study of MAP to analyze the structure of MAP, to design an MAP gene based on the analyzed MAP structures, and to synthesize it. The present inventors have also made the most of gene recombination and have developed a method for producing MAP by introducing foreign genes into e.g. E.coli to produce MAP therein.

This method, however, suffers from the disadvantage that MAP produced and stored in E.coli inhibits biosynthesis of host cell proteins. Therefore, growth of E.coli is inhibited and the amount of MAP produced therein does not readily increase, which limits the production of MAP.

On the other hand, in order to separate a protein which accumulates in E.coli, a method is conventionally known to make a gene encoding a signal peptide combine with a gene coding for the objective protein and induce the produced protein to secrete. Although many signal peptides are known, it requires practical experiments at present to know whether the desired effect can be obtained.

SUMMARY OF THE INVENTION

It is an object of the invention to provide a method for producing MAP which does not inhibit the growth of E.coli.

It is also an object of the invention to provide a gene which codes for MAP and is utilized as a foreign gene for said method for producing MAP.

It is a further object of the invention to provide a recombinant plasmid which contains said gene and is utilized as a vector in said method for producing MAP.

A method for producing MAP according to the present invention utilizes a nucleic acid molecule which is formed by ligating a gene coding for the outer membrane protein OmpA signal peptide as shown in FIG. 1 with the MAP gene having a nucleotide sequence as shown in FIG. 2 at its 5'-terminal. The foreign gene is then introduced into E.coli. This introduction uses a recombinant plasmid which is formed by integrating said foreign gene into a plasmid having an E.coli expression system. The E.coli thus transformed produces MAP by expression of said gene, and also extracellulary transfers the produced MAP. Therefore, no MAP accumulates in E.coli and growth of E.coli is not inhibited.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

FIG. 1 shows a signal sequence of OmpA and a nucleotide sequence coding for the signal sequence;

FIG. 2 shows a nucleotide sequence of a synthetic gene coding for MAP;

FIG. 3 shows a nucleotide sequence of a synthetic DNA linker; and

FIGS. 4A to 4C show processes for forming a DNA vector including an MAP gene and gene coding for the signal sequence according to an preferable embodiment of the present invention.

DETAILED DESCRIPTION OF THE PREFERRED EMBODIMENTS

Figure 4A:
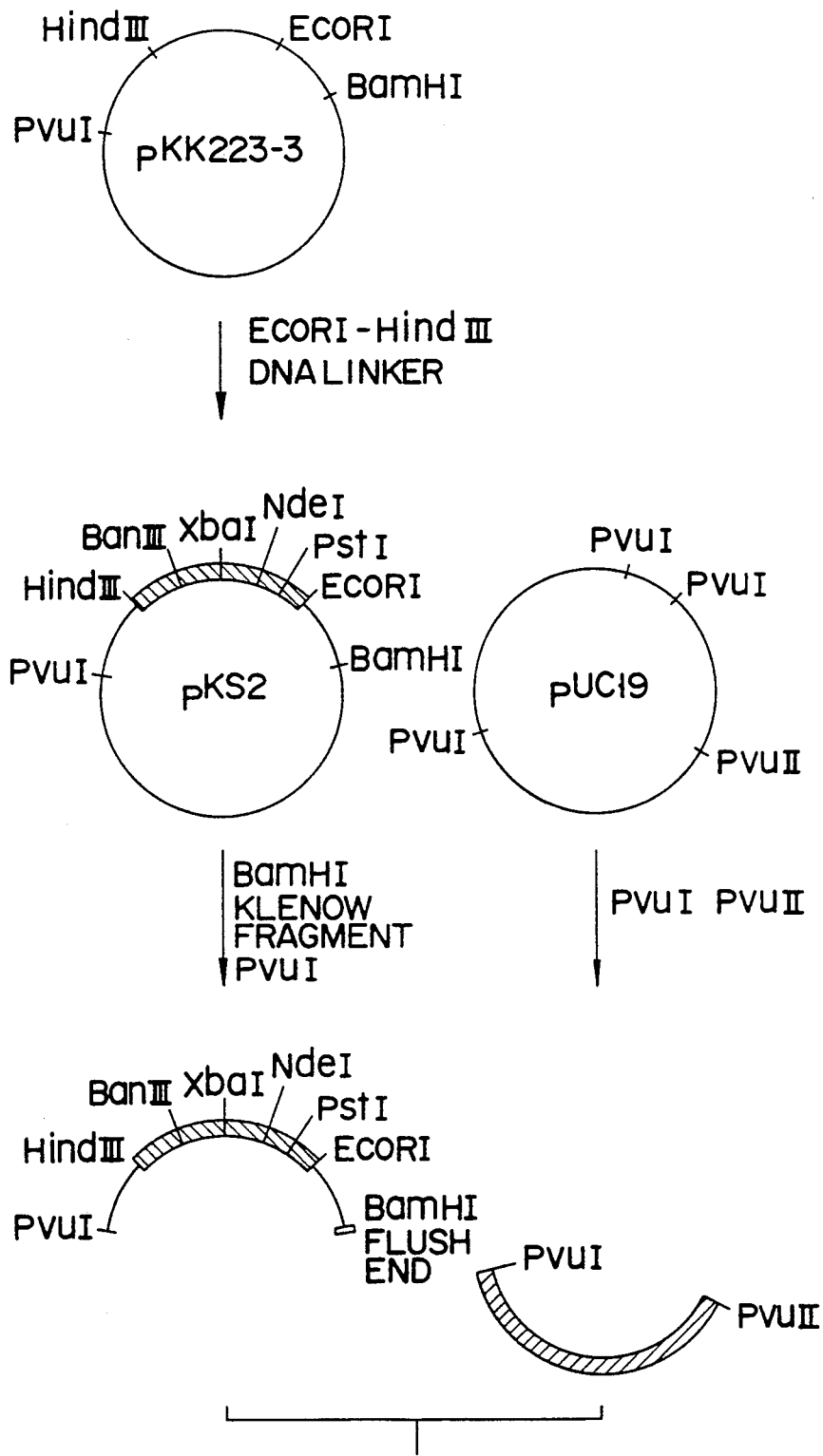

The preferable E.coli plasmid for utilizing as a vector in the invention maintains a number of copies in E.coli and includes a gene marker which makes the bacteria resistant against antibiotics, etc.. Examples of the plasmids are pUC19, pBBR322, pKK223-3 and pTTQ19, and other plasmids obtained by fusing some plasmids or by partially deleting bases from any one of the plasmids can also be used. An example of a fused plasmid is formed by fusing a region including replication origin (ori) and a part of ampicillin-resistance gene region (Ap) (i.e. a fragment obtained by digesting with restriction enzyme PvuI and PvuII) of pUC19, and a part of Ap, tac promoter region and rrnBT$_4$T$_2$ terminator region (i.e. a fragment obtained by complete digestion using PvuI and partial digestion using BamHI) of pKK223-3.

A vector for introducing a foreign gene which is to be expressed in E.coli generally requires the following DNA sequences other than the gene to be introduced;

(a) a region for operating transcription (operator)

(b) a region for promoting initiation of gene transcription (promoter);

Examples of promoters which are known to manifest in E.coli are the N25 promoter and the $P_L$ promoter, both of which are derived from coliphage, etc.. The $P_L$ promoter is derived from E.coli lambda-phage and is known to be repressed by a control protein which is called cI. The cI includes temperature-sensitive mutant, called $cI_{857}$, which represses the $P_L$ promoter at 30° C., like the cI, but loses its repressing ability at 42° C., causing the $P_L$ promoter to turn on. Accordingly, if an expression vector introduced in E.coli includes both the $P_L$ promoter and the $cI_{857}$ repressor gene, E.coli can be grown by culturing it at 30° C. such that $P_L$ promoter is repressed. Also, the $P_L$ promoter can be turned on to initiate transcription of the gene by culturing E.coli at 42° C.

The $P_L$ promoter can be obtained by digesting lambda-phage gene or disclosed pPL-lambda plasmid with the restriction enzymes BamHI and HpaI. The $cI_{857}$ repressor gene can be obtained by digesting the DNA of a lambda-phage mutant ($cI_{857}$, Sam 7) with the restriction enzyme BglII and BanIII.

(c) a region for instructing termination of transcription (terminator)

Examples of known terminators are tLI terminator derived from coliphage, $rrnBT_1T_2$ terminator derived from ribosome gene of E.coli, etc..

(d) a region for instructing the initiation position of transcription after transcription into mRNA (Shine-Dalgarno, SD sequence)

A sequence which is common to the construction gene of E coli can be used as SD sequence.

(e) methionine codon which is linked to the SD sequence and is for initiation of translation (ATG)

A. Formation of E.coli expression vector

An expression vector derived from plasmid DNA can be formed by deletion or insertion of a specific region from the plasmid DNA. The deletion and insertion can be performed by cleaving the plasmid at specific sites and combining the resultant fragments by means of an appropriate treatment. Specifically, appropriate utilization of synthetic DNA fragments enables restriction enzyme sites, SD sequence, gene for coding amino acid sequence of protein, etc. which are not included in the original plasmid DNA to be introduced.

For example, by making the DNA fragment and its complementary chain which are shown in FIG. 3 and including XbaI and BanIII sites that are not included in plasmid pKK223-3 to combine with a cleavage fragment (a large fragment) which is obtained by digesting the pKK223-3 with EcoRI-HindIII, the restriction sites of XbaI and BanIII can be introduced in the pKK223-3. Additionally, by utilizing this pKK223-3 which includes restriction sites of XbaI and BanIII and a fully synthetic MAP gene also having XbaI and BanIII sites in its 5'- and 3'-terminas respectively, the fully synthetic MAP gene can be introduced into the plasmid pKK223-3. Further, SD sequence and a codon coding for a methionine residue which is required for initiating transcription of the gene can also be introduced into said plasmid at this time. Moreover, since the restriction site of NdeI (CATATG) includes a methionine codon (ATG), a gene coding for other proteins can be introduced through this site.

Required DNA fragments can be synthesized by a DNA synthesizer. An expresion vector is formed by combining DNA fragments obtained by the DNA synthesizer, those obtained by restriction enzyme cleavage, and such a DNA fragment as needed obtained by converting a cohesive end into a flush end utilizing T4 DNA polymerase, DNA polymerase Klenow fragment, etc.. Each fragment can be combined by T4 DNA ligase or a commercially available ligation kit including the DNA ligase.

B. Formation of Secretory MAP Gene

OmpA is an outer membrane protein of E.coli and comprises a signal sequence as shown in FIG. 1. A nucleotide sequence of a gene coding for this signal sequence is also shown in FIG. 1. This signal sequence functions to make OmpA to secrete from E.coli. Therefore, by linking this signal sequence to the N-terminal end of another protein, the protein can be transferred outside from inside of the E.coli. For example, by linking the signal sequence shown in FIG. 1 to N-terminal of MAP, MAP can be secreted from E.coli.

Further a gene for coding the signal sequence has the first methionine codon included in a part of said NdeI sites, and thus a foreign gene can be introduced into an expression vector having the NdeI site which is downstream from a promoter.

FIG. 1 also shows a sequence of three amino acids of the MAP N-terminal end and a DNA sequence corresponding thereto.

C. Production of MAP utilizing E.coli transformant.

According to the method as said, an expression vector can be prepared which contains the $P_L$ promoter, $cI_{857}$ gene, and a gene for coding a protein. This vector can be further utilized to transform E.coli by a disclosed method, e.g. by the calcium chloride method.

A medium for culturing the transformants may contain carbon source, nitrogen source, minerals and, on an as-needed basis, minor organic nutrition sources such as amino acids, vitamins, etc..

The transformants can be cultured e.g. in a liquid medium under the aerobic condition by e.g. stirring with aeration, with 6.5-8.5 of pH maintained. The cells are cultured for several hours to about four days to produce MAP and to allow it accumulate in a medium.

Next, the medium containing MAP obtained as said is condensed. The resultant solution is subjected to an appropriate combination of salting out, ion exchange chromatography, gel filtration, affinity chromatography, etc. to purify MAP.

One example is that a MAP gene or a gene obtained by combining MAP gene and a gene for coding signal sequence is inserted into an expression vector including $P_L$ promoter and $cI_{857}$ gene, and this vector is introduced into E.coli, allowing generation of MAP, firstly by culturing the transformed E.coli under the aerobic condition at 30° C. to fully grow the bacteria, and immediately after that increasing a culture temperature to 42° C., followed by further culture under the aerobic condition. MAP can be thus efficiently produced.

MAP thus produced can be determined by an immunological technique utilizing anti-MAP antibodies.

Although the following is to describe the present invention in detail with reference to preferable embodiments, it is to be understood that the invention is not restricted to the description. To understand the following embodiments, processes of forming DNA vector in the embodiments are shown in FIGS. 4A to 4C.

A Step of Inserting A Synthetic DNA Fragment into Plasmid pKK223-3

A DNA linker containing restriction enzyme sites, SD sequence, methionine codon, and coding N-terminal amino acid sequence of MAP shown in FIG. 3 was inserted into plasmid pKK223-3 (manufactured by Pharmacia Japan Co., Ltd.).

One micro gram of pKK223-3 was incubated in High Buffer (a mixture of 50mM Tris·HCl [pH7.5]-100mM of NaCl-1mM of MgCl) containing 10 units of each restriction enzyme of EcoRI and HindIII (manufactured by Nippon Gene Co, Ltd.) at 37° C. for one hour for digestion. The obtained solution was subjected to phenol-chloroform treatment and ethanol precipitation to collect DNA. The phenol-chloroform treatment is described in detail was follows. Firstly, phenol was saturated with a mixture (hereinafter abbreviated as TE) of 10mM of Tris HCl (pH8.0) and 1mM of ethylenediamine tetra acetic acid (EDTA). The equivalent volume of the resultant phenol solution was added to the obtained DNA solution for mixing, and the resultant mixture was centrifuged to collect a aqueous phase containing DNA. Next, an equivalent volume of chloroform was added to this aqueous phase for further mixing, and the resultant mixture was centrifuged to collect an aqueous phase containing DNA. Ethanol precipitation is described in detail as follows. Firstly, to the obtained solution containing DNA, 5M of sodium chloride of 1/20-fold volume and ethanol of 2-fold volume were added, and the resultant mixture was cooled at −70° C. for thirty minutes. Next, this solution was centrifuged at high speed to separate the obtained precipitant.

Two kinds of single-stranded synthetic DNA linkers of complementary nucleotide sequences shown in FIG. 3 were prepared by utilizing the DNA synthesizer (manufactured by Applied Biosystems Japan Company, 381A-type) according to the phosphoroamidide method. One microgram of each obtained synthetic linker was incubated in 100 μl of a kinase solution (a mixture of 50mM of Tris HCl [pH7.6], 10mM of MgCl$_2$, 5mM of dithiothreitol, 0.1mM of spermidine, 0.1mM of EDTA, and 1mM of ATP) containing 10 units of T4 kinase (manufactured by Toyobo Co., Ltd.) at 37° C. for one hour to add phosphoric acid to 5′-terminal of the linkers. After that, the obtained single-stranded DNA was converted into double-stranded DNA by annealing. This annealing was performed by mixing the obtained reacted solutions, heating the resultant mixture at 60° C. for twenty minutes, and allowing it to stand at room temperature for twenty minutes. Next, the resultant solution was subjected to ethanol precipitation, and then the precipitate was dissolved in 10 μl of TE.

To 5 μl of the thus obtained solution containing double-stranded synthetic DNA, 2.5 μl of (ca. 0.5 μg) of pKK223-3 cleavage product was added and the mixture was ligated at 10° C. for two hours utilizing the ligation kit (manufactured by Takara Syuzo Co., Ltd). Plasmid pKS2 was then obtained by introducing the synthetic DNA linker into the plasmid pKK223-3.

A Step of Converting Replication Origin of pKS2 to that of plasmid pUC19 Type Two microgram of plasmid pKS2 and restriction enzyme BamHI were incubated at 37° C. for one hour in 50 μl of High Buffer for digestion. Next, the obtained solution was subjected to phenol-chloroform treatment and ethanol precipitation to collect cleaved DNA. The obtained precipitate was added to 25 μl of Klenow solution (which is obtained by adding 0.1mM of each co-factor dATP, dGTP, dCTP and TTP to a mixture of 50mM of Tris·HCl [pH7.2], 10mM of MgS04, 0.1mM of dithiothreitol, and bovine serum albumin of 50 μg/ml), and the resultant solution was incubated at 22° C. for 30 minutes to convert a cohesive end of the DNA to a flush end. After reaction, the solution was heated at 70° C. for five minutes, followed by phenol-chloroform treatment and ethanol precipitation to collect DNA. The collected DNA was further cleaved by dissolving it in 50 μl of High Buffer containing 10 units of restriction enzyme PvuI (manufactured by Toyobo Co., Ltd.) at 37° C. for one hour. The cleaved DNA was collected by phenolchloroform treatment followed by ethanol precipitation.

Separately, 1 μg of plasmid pUC 19 (manufactured by Takara Syuzo Co., Ltd.) was incubated in 50 μl of High Buffer containing 10 units of each restriction enzyme PvuI (manufactured by Toyobo Co., Ltd.) and PvuII (manufactured by Nippon Gene Co., Ltd.) at 37° C. for two hours to cleave pUC19. The cleaved DNA fragments were collected by phenol-chloroform treatment, followed by ethanol precipitation.

The DNA fragments (larger fragments) derived from pKS2 and DNA fragments derived from pUC19 both of which were obtained as mentioned were dissolved in 10 μl of TE, respectively. After that, each 3.5 μl of the TE solutions were mixed and the fragments was ligated at 10° C. for one hour utilizing the ligation kit (manufactured by Takara Syuzo Co., Ltd.) to obtain plasmid pKS3. This pKS3 comprises the replication origin of pUC19 and the large fragment of pKS2 which are combined therein.

Step of Inserting P$_L$ Promotor into pKS3

Two micrograms of pKS3 was incubated in 50 μl of High Buffer containing 10 units of a restriction enzyme PstI (manufactured by Nippon Gene Co., Ltd.) at 37° C. for one hour for digestion. The cleaved DNA fragment was collected by phenol-chloroform treatment followed by ethanol precipitation. The collected DNA fragment was incubated in 20 μl of polymerase solution (which was obtained by adding 0.1mM of each co-factor of dATP, dGTP, dCTP and TTP to a mixture of 33mM of Tris·HCl [pH7.9], 66mM of potassium phosphate, 10mM of magnesium acetate, 0.5mM of dithiothreitol, and 0.1mg/ml of bovine serum albumin) containing 2.5 units of T4 DNA polymerase (manufactured by Toyobo Co., Ltd.) at 37° C. for five minutes to convert a cohesive end of the DNA fragment to a flush end. Next, 1 μl of 0.5M EDTA was added to the resultant solution, and the obtained mixture was subjected to phenol-chloroform treatment and further ethanol precipitation to collect DNA. The collected DNA was incubated in 50 μl of High Buffer containing 10 units of restriction enzyme BamHI (manufactured by Nippon Gene Co., Ltd.) at 37° C. for one hour for additional digestion.

Separately, 1 μg of pPL-lambda (manufactured by Pharmacia Co., Ltd.) was incubated in 50 μl of High Buffer containing 10 units of each restriction enzyme BamHI and HpaI (both manufactured by Nippon Gene Co., Ltd.) at 37° C. for one hour for digestion. Next, the mixture was subjected to phenol-chloroform treatment and the following ethanol precipitation to collect DNA fragment containing the $P_L$ promotor.

The DNA fragment derived from pKS3 and the DNA fragment containing the $P_L$ promoter were dissolved in 10 μl of TE, respectively. Next, 3.5 μl of each solution obtained as said were mixed, and the DNA fragments therein were ligated utilizing the ligation kit (manufactured by Takara Syuzo Co., Ltd.). After that, the resultant DNA was utilized to transform E.coli (strain HB101). From the obtained transformants, plasmid pSH4 was prepared. This plasmid pSH4 is the plasmid which was formed by inserting the $P_L$ promotor into pKS3.

A Step of Cleaving out $cI_{857}$ Gene form Lambda-phage DNA

Two micrograms of lambda-phage (lambda, $cI_{857}$, Sam7) DNA (manufactured by Takara Syuzo Co., Ltd.) was incubated in 50 μl of High Buffer containing 10 units of each restriction enzyme BglII (manufactured by Nippon Gene Co., Ltd.) and BanIII (manufactured by Toyobo Co., Ltd.) at 37° C. for two hours for digestion. The obtained DNA fragments were collected by phenol-chloroform treatment followed by ethanol precipitation.

Meanwhile, 1 μg of plasmid pHSG397 (manufactured by Takara Syuzo Co., Ltd.) was incubated in 50 μl of High Buffer containing 10 units of each restriction enzyme BamHI (Nippon Gene Co., Ltd.) and BanIII (manufactured by Toyobo Co., Ltd.) at 37° C. for one hour for digestion. Next, to the mixture, 2 μl (1 unit) of alkaline phosphatase (manufactured by Toyobo Co., Ltd.) was added, and the resultant mixture was allowed to heat at 60° C. for 30 minutes for dephosphorylation at 5'-terminal of the DNA. After that, the DNA was collected by phenolchloroform treatment and the following ethanol precipitation.

The lambda-phage DNA cleavage product and the pHSG397 cleavage product both of which were thus obtained were dissolved in each 10 μl of TE. Next, 3 5 μl of each solution were mixed and the DNA cleavage products therein were ligated by reacting the mixture at 10° C. for two hours utilizing the ligation kit (manufactured by Takara Syuzo Co., Ltd.). The obtained DNA was utilized to transform E.coli (strain HB101), and plasmid DNA was purified from the obtained transformants. This plasmid DNA is pHSGcI$_{857}$ formed by inserting BglII-BanIII fragment of ca.1100 base pairs including $cI_{857}$ into pHSG397.

A Step of Inserting $cI_{857}$ into pSH4

Two micrograms of pHSGcI$_{857}$ was incubated in 50 μl of High Buffer containing 10 units of each restriction enzyme XhoI (manufactured by Nippon Gene Co., Ltd.) and BanIII (manufactured by Toyobo Co., Ltd.) at 37° C. for one hour for digestion. The cleaved DNA fragments were collected by phenol-chloroform treatment and the following ethanol precipitation. The collected DNA was incubated in 25 μl of Klenow solution containing two units of Krenow fragment at 22° C. for 30 minutes to convert a cohesive end of the DNA to a flush end. Next, the resultant solution was heated at 70° C. for five minutes and subjected to phenol-chloroform treatment and the following ethanol precipitation to collect the DNA.

On the other hand, 1 μg of pSH4 was incubated in 50 μl of High Buffer containing 10 units of restriction enzyme BamHl (manufactured by Nippon Gene Co., Ltd.) at 37° C. for one hour for digestion. The cleaved DNA was collected by phenol-chloroform treatment and the following ethanol precipitation. The collected DNA was incubated in 25 μl of Klenow solution containing 2 units of Klenow fragment at 22° C. for 30 minutes to convert a cohesive end of the DNA to a flush end. Next, the resultant solution was heated at 70° C. for five minutes, and subjected to phenol-chloroform treatment and the following ethanol precipitation to collect the resultant DNA.

The DNA fragments including $cI_{857}$ and the cleaved pSH4 fragments both of which were thus obtained were dissolved in 10 μl of TE, respectively. Next, 3.5 μl of each solution was mixed and the DNA fragments were ligated by reacting the solution at 10° C. for two hours utilizing the ligation kit (manufactured by Takara Syuzo Co., Ltd.). The obtained DNA was utilized to transform E.coli (strain HB101), and plasmid DNA was purified from the obtained transformants. The obtained plasmid is pSH5 formed by inserting $cI_{857}$ into plasmid pSH4.

A Step of Inserting a Complete Synthetic MAP Gene into pSH5

Two micrograms of pSH5 was incubated in 50 μl of High Buffer containing 10 units of each restriction enzyme XbaI (manufactured by Nippon Gene Co., Ltd.) and BanIII (manufactured by Toyobo Co., Ltd.) at 37° C. for one hour for digestion. The resultant solution was subjected to phenol-chloroform treatment and the following ethanol precipitation to collect the cleaved DNA.

Meanwhile, 2 μg of pMHI was digested and the cleaved DNA was collected by the same manner as said for pSH5. The pMHI here is a synthetic plasmid formed by inserting a complete synthetic MAP gene into the plasmid pUC19.

The DNA fragments derived from pSH5 and the fragments from pMHI thus obtained were dissolved into 10 μl of each TE, respectively. Next, 3.5 μl of each solution was mixed and the DNA fragments therein were ligated by reacting the resultant mixture at 10° C. for one hour utilizing the ligation kit (manufactured by Takara Syuzo Co., Ltd.). The combined DNA was used to transform E.coli (strain N99cI+), and plasmid DNA was purified from the obtained transformants. This plasmid is pSH6 formed by inserting a fragment of the complete synthetic MAP gene, which obtained by reacting with XbaI and BanIII, into the plasmid pSH5.

A Step of Inserting Signal Sequence Gene of OmpA into pSH6

Each single-stranded DNA of complementary DNA fragments having a base sequences shown in FIG. 1 was synthesized according to phosphoroamidide method utilizing a DNA synthesizer (manufactured by Applied Biosystems Japan, 381A type). One microgram of each synthesized single-stranded DNA was incubated in 50 μl of said kinase solution containing 10 units of T4 kinase (manufactured by Toyobo Co., Ltd.) at 37° C. for one hour to horylate phosphorylate 5'-terminal of the DNA. Each solution containing the phosphorylated single-stranded DNA were mixed and the resultant solution was heated at 60° C. for 20 minutes and allowed to stand at room temperature for 20 minutes for annealing to obtain double-stranded DNA. The obtained double-stranded DNA was collected by ethanol precipitation and dissolved in 10 μl of TE.

On the other hand, 1 μg of the plasmid pSH6 was incubated in 50 μl of High Buffer containing 10 units of each restriction enzyme NdeI and XbaI (both manufactured by Nippon Gene Co., Ltd.) at 37° C. for one hour for digestion. The cleaved DNA was collected by subjecting the reacted solution to phenol-chloroform treatment and the following ethanol precipitation. The collected DNA was further dissolved in 10 μl of TE.

Three point five micro liter of the TE solution containing the annealed synthetic DNA and also 3.5 μl of the TE solution containing the cleaved pSH6 was mixed. The mixture was reacted at 10° C. for two hours by utilizing the ligation kit (manufactured by Takara Syuzo Co., Ltd.) to combine the synthetic DNA and the cleaved DNA. The combined DNA was used to transform E.coli (strain N99cI+), and plasmid DNA was purified from the obtained transformants. This plasmid is plasmid pSH7 formed by inserting the gene of OmpA signal sequence into pSH6.

Expression of MAP Utilizing E.coli transformed with The Plasmid pSH6

E.coli (strain MM294) was transformed by the plasmid pSH6. The obtained transformants were cultured in 5 ml of LB medium (a mixture of 1% bact.trypton, 0.5% bact.yeast extract, 1% sodium chloride, and 0.1% glucose) containing 50 μg/ml of ampicillin at 30° C. under the aerobic condition overnight. Next, the medium was added into M9CA medium (a mixture of 6g/l of disodium phosphate, 3g/l of potassium phosphate, 0.5g/l of sodium chloride, lg/l of ammonium chloride, 2mM of magnesium sulphate, 0.lmM of calcium chloride, and 2g/l of glucose) containing 50 μg/ml of ampicillin and 4 μg/ml of thiamine hydrochloride to achieve a final concentration of 1%. The resultant solution was cultured at 30° C. under the aerobic condition. Growth rate of the transformants was almost the same as that of *E.coli* transformants (strain MM294) which was transformed with plasmid pSH5 containing no MAP gene. It is apparent from this fact that the plasmid pSH6 did not affect the growth of *E.coli.*

When the absorbance of the medium at 550nm achieved 0.8, M9CA medium which had already been heated to 55° C. was added to the medium in equivalent volume to accelerate the production of MAP. After that, the solution was further cultured at 42° C. under the aerobic condition to have MAP accumulated in *E.coli* bodies.

After culture was terminated, the *E.coli* bodies were collected by centrifugation and suspended in 0.9% aqueous NaCl solution which is equivalent to the medium in volume. This suspension was further centrifuged to collect the *E.coli* bodies. The collected bodies were further suspended in 0.9% aqueous sodium chloride solution, followed by braking by means of a ultra sonic vibrator. The obtained sample was subjected to enzyme-linked immunosorbent assay (ELISA). The result was that 20 μg/l of MAP was produced.

Expression of MAP Utilizing *E.coli* Transformed with Plasmid pSH7

*E.coli* (strain MM294) was transformed by the plasmid pSH7. The obtained transformants were cultured with shaking in 5 ml of LB medium containing 50 μg/ml of amplicillin under the aerobic condition at 30° C. overnight in the same manner as for pSH6. Next, the medium was added into M9CA medium containing 50 μg/ml of ampicillin and 4 μg/ml of thiamine hydrochloride to achieve a final concentration of 1%, followed by culture at 30° C. under the aerobic condition in the same manner as for pSH6. The growth rate of the transformants was almost the same as that of *E.coli* transformants (strain MM294) which was transformed with the plasmid pSH5 containing no MAP gene. This fact reveals that the plasmid pSH7 did not affect the growth of the *E.coli.*

When absorbance of the medium at 550nm achieved 0.8, M9CA medium which had been already heated to 55° C. was added to the medium in equivalent volume to accelerate MAP production. After that, the resultant medium was further cultured at 42° C. under the aerobic condition to have MAP accumulated in the medium.

After the culture was terminated, the *E.coli* bodies were separated by centrifugation, and the residual solution was dialyzed with water. The dialyzed solution was subjected to an immunological analysis (ELISA) utilizing anti-MAP antibodies to detect extracellularly 200 μg/l of MAP in the solution. Additionally, western blotting analysis was performed to confirm presence of a protein having the same molecular weight as that of MAP in the solution.

Additional advantages and modifications will readily occur to those skilled in the art. Therefore, the invention in its broader aspects is not limited to the specific details, and illustrated examples shown and described herein. Accordingly, various modifications may be made without departing from the spirit or scope of the general inventive concept as defined by the appended claims and their equivalents.

What is claimed is:

1. A DNA fragment comprising the following base sequence coding for Mirabilis antiviral protein (MAP)

```
GCGCCTACTC  TAGAAACCAT  CGCTTCTCTG
CGCGGATGAG  ATCTTTGGTA  GCGAAGAGAC

GACCTGAACA
                          CTGGACTTGT

ACCCGACCAC  CTACCTGTCT  TTCATAACGA
TGGGCTGGTG  GATGGACAGA  AAGTATTGCT

ATATCCGTAC
                          TATAGGCATG

GAAAGTCGCA  GACAAAACCG  AACAGTGTAC
CTTTCAGCGT  CTGTTTTGGC  TTGTCACATG

CATCCAGAAA
                          GTAGGTCTTT

ATCTCTAAAA  CCTTCACCCA  GCGTTACTCT
TAGAGATTTT  GGAAGTGGGT  CGCAATGAGA

TACATAGACT
                          ATGTATCTGA

TGATCGTGAG  CTCGACGCAG  AAAATCACCC
ACTAGCACTC  GAGCTGCGTC  TTTTAGTGGG

TAGCTATCGA
                          ATCGATAGCT

CATGGCTGAC  CTGTACGTTC  TGGGTTACTC
GTACCGACTG  GACATGCAAG  ACCCAATGAG

TGACATCGCT
                          ACTGTAGCGA
```

-continued

AATAACAAGG GTCGTGCTTT CTTCTTCAAA
TTATTGTTCC CAGCACGAAA GAAGAAGTTT

GACGTGACTG
CTGCACTGAC

AGGCTGTTGC GAACAATTTC TTCCCGGGAG
TCCGACAACG CTTGTTAAAG AAGGGCCCTC

CTACAGGTAC
GATGTCCATG

TAATCGTATC AAATTAACCT TTACAGGTTC
ATTAGCATAG TTTAATTGGA AATGTCCAAG

TTATGGCGAT
AATACCGCTA

CTCGAGAAAA ACGGCGGACT ACGTAAGGAC
GAGCTCTTTT TGCCGCCTGA TGCATTCCTG

AATCCCCTAG
TTAGGGGATC

GTATCTTCCG TCTGGAAAAC TCGATAGTTA
CATAGAAGGC AGACCTTTTG AGCTATCAAT

ACATTTATGG
TGTAAATACC

CAAAGCTGGT GACGTTAAAA AACAGGCTAA
GTTTCGACCA CTGCAATTTT TTGTCCGATT

ATTCTTCTTA
TAAGAAGAAT

CTGGCTATCC AGATGGTTTC GGAGGCTGCG
GACCGATAGG TCTACCAAAG CCTCCGACGC

CGCTTTAAGT
GCGAAATTCA

ATATCAGTGA CAAAATCCCG TCTGAAAAAT
TATAGTCACT GTTTTAGGGC AGACTTTTTA

ACGAAGAAGT
TGCTTCTTCA

TACCGTTGAC GAATACATGA CCGCTCTGGA
ATGGCAACTG CTTATGTACT GGCGAGACCT

AAACAACTGG
TTTGTTGACC

-continued

GCTAAACTGT CTACGGCCGT ATACAACTCT
CGATTTGACA GATGCCGGCA TATGTTGAGA

AAGCCTTCTA
TTCGGAAGAT

CCACCACCGC TACCAAATGT CAGCTGGCTA
GGTGGTGGCG ATGGTTTACA GTCGACCGAT

CCTCTCCGGT
GGAGAGGCCA

TACCATCTCT CCGTGGATAT TCAAAACCGT
ATGGTAGAGA GGCACCTATA AGTTTTGGCA

CGAGGAAATC
GCTCCTTTAG

AAACTGGTTA TGGGTCTGCT TAAGTCTTCT
TTTGACCAAT ACCCAGACGA ATTCAGAAGA

TAATAA
ATTATT wherein said fragment also includes the following sequence coding for an OmpA signal sequence operably linked to said MAP gene

TATGAAAAAGACAGCTATCGCGATTGCAGT
ACTTTTTCTGTCGATAGCGCTAACGTCA

GGCACTGGCT
CCGTGACCGA

GGTTTCGCTACCGTAGCGCAGGCC
CCAAAGCGATGGCATCGCGTCCGG

GCGCCTACT
CGCGGATGAGATC.

2. A recombinant plasmid including a $P_L$ promoter derived from Escherichia coli λ-phage, a $CI_{857}$ repressor gene, and the DNA fragment claimed in claim 1 in this order, wherein said $P_L$ promoter and said $CI_{857}$ repressor gene are positioned upstream of the DNA fragment claimed in claim 1.

3. An Escherichia coli transformant containing the plasmid of claim 2.

4. A method for producing Mirabilis antiviral protein comprising the steps of:

(a) culturing the Escherichia coli trnasformants of claim 3 to produce the Mirabilis antiviral protein and extracellularly secreting the Mirabilis antiviral protein so produced; and (b) separating and purifying the Mirabilis antiviral protein which is extracellularly secreted.

* * * * *